United States Patent
Lee et al.

(10) Patent No.: US 7,622,848 B2
(45) Date of Patent: Nov. 24, 2009

(54) TRANSDUCER ASSEMBLY WITH Z-AXIS INTERCONNECT

(75) Inventors: Warren Lee, Niskayuna, NY (US); Charles Edward Baumgartner, Schenectady, NY (US); Douglas Glenn Wildes, Ballston Lake, NY (US); Robert Stephen Lewandowski, Amsterdam, NY (US)

(73) Assignee: General Electric Company, Niskayuna, NY (US)

( * ) Notice: Subject to any disclaimer, the term of this patent is extended or adjusted under 35 U.S.C. 154(b) by 609 days.

(21) Appl. No.: 11/327,779

(22) Filed: Jan. 6, 2006

(65) Prior Publication Data

US 2007/0157732 A1    Jul. 12, 2007

(51) Int. Cl.
    *H01L 41/08* (2006.01)
(52) U.S. Cl. ........................................ 310/334
(58) Field of Classification Search .......... 310/322, 310/334, 366
    See application file for complete search history.

(56) References Cited

U.S. PATENT DOCUMENTS

| | | | | |
|---|---|---|---|---|
| 4,385,255 A | * | 5/1983 | Yamaguchi et al. | 310/335 |
| 4,616,152 A | * | 10/1986 | Saito et al. | 310/334 |
| 4,676,106 A | * | 6/1987 | Nagai et al. | 73/625 |
| 4,686,408 A | * | 8/1987 | Ishiyama | 310/334 |
| 5,267,221 A | | 11/1993 | Miller et al. | 367/140 |
| 5,329,498 A | * | 7/1994 | Greenstein | 367/155 |
| 5,592,730 A | | 1/1997 | Greenstein et al. | 29/594 |
| 6,087,761 A | * | 7/2000 | Lorraine et al. | 310/334 |
| 6,087,762 A | * | 7/2000 | Corbett et al. | 310/334 |
| 6,100,626 A | * | 8/2000 | Frey et al. | 310/334 |
| 6,308,389 B1 | * | 10/2001 | Tezuka | 29/25.35 |
| 6,341,408 B2 | * | 1/2002 | Bureau et al. | 29/25.35 |
| 6,541,896 B1 | | 4/2003 | Piel, Jr. et al. | 310/334 |
| 6,625,854 B1 | | 9/2003 | Sudol et al. | 29/25.35 |
| 6,736,779 B1 | * | 5/2004 | Sano et al. | 600/447 |
| 7,017,245 B2 | * | 3/2006 | Baumgartner et al. | 29/25.35 |
| 7,229,292 B1 | * | 6/2007 | Haider et al. | 439/67 |
| 2003/0028105 A1 | * | 2/2003 | Miller | 600/437 |
| 2003/0085635 A1 | * | 5/2003 | Davidsen | 310/334 |
| 2003/0153834 A1 | * | 8/2003 | Miller | 600/459 |
| 2004/0002656 A1 | * | 1/2004 | Sheljaskow et al. | 600/459 |
| 2004/0011134 A1 | * | 1/2004 | Sato | 73/632 |
| 2004/0100163 A1 | | 5/2004 | Baumgartner et al. | 310/334 |
| 2004/0254471 A1 | | 12/2004 | Hadjicostis et al. | 600/459 |
| 2005/0113699 A1 | * | 5/2005 | Haugen et al. | 600/459 |
| 2005/0165314 A1 | * | 7/2005 | Tanaka | 600/459 |
| 2005/0225210 A1 | | 10/2005 | Englund et al. | 310/334 |

* cited by examiner

*Primary Examiner*—Thomas M Dougherty
(74) *Attorney, Agent, or Firm*—Patrick K. Patnode

(57) ABSTRACT

A composite structure of a z-axis interconnect is presented. The composite structure includes a plurality of layers of backing material alternatingly arranged between a plurality of interconnect layers, where the plurality of interconnect layers is configured to facilitate coupling the composite structure of the z-axis interconnect to a transducer array, where the composite structure of z-axis interconnect is configured for use in an invasive probe.

18 Claims, 14 Drawing Sheets

TRANSDUCER ASSEMBLY WITH Z-AXIS INTERCONNECT

BACKGROUND

The invention relates generally to transducers, and more specifically to a transducer assembly for real-time three-dimensional imaging in space-critical applications.

Transducers, such as acoustic transducers, have found application in medical imaging where an acoustic probe is held against a patient and the probe transmits and receives ultrasound waves, which in turn may facilitate the imaging of the internal tissues of the patient. For example, transducers may be employed to image the heart of the patient.

Heart rhythm problems or cardiac arrhythmias are a major cause of mortality and morbidity. Atrial fibrillation is one of the most common sustained cardiac arrhythmias encountered in clinical practice. Cardiac electrophysiology has evolved into a clinical tool to diagnose these cardiac arrhythmias. As will be appreciated, during electrophysiological studies, probes, such as multipolar catheters, are positioned inside the anatomy, such as the heart, and electrical recordings are made from the different chambers of the heart.

Catheter-based techniques used in interventional procedures generally involve inserting a probe, such as an imaging catheter, into a vein, such as the femoral vein. Unfortunately, conventional cardiac interventional procedures such as ablation of atrial fibrillation are complicated due to the lack of an efficient method to visualize interventional devices and cardiac anatomy in real-time.

Techniques, such as transthoracic imaging have been employed to overcome the drawbacks of the conventional cardiac interventional procedures. Transthoracic imaging techniques typically necessitate placement of a transceiver against the chest of a patient and the use of this transceiver to image the heart. However, the presence of bones and other tissue types interposed between the transceiver and the heart during the transthoracic imaging procedure prevents the formation of a sufficiently detailed image of the heart. Alternate techniques such as transesophageal imaging procedures have also been utilized to facilitate imaging of the heart. These transesophageal techniques typically involve the insertion of a transceiver into the esophagus of the patient. Although transesophageal imaging positions the transceiver closer to the heart, a drawback of this procedure is that transesophageal imaging necessitates rendering the patient unconscious by way of a general anesthetic. However, as will be appreciated, it is highly desirable to have a conscious patient to facilitate imaging of the heart.

The drawbacks associated with the above mentioned techniques may be circumvented via the use of intracardiac echocardiography (ICE). Intracardiac echocardiography is an emerging catheter imaging technology employed to guide interventional procedures such as catheter positioning and ablation, for example. Furthermore, intracardiac echocardiography typically uses sound waves to produce images of the heart. Additionally, with intracardiac echocardiography, a probe, such as a miniaturized ultrasound tipped catheter, may be utilized to obtain images of the heart.

Unfortunately, currently available commercial catheter-based intracardiac probes are restricted to two-dimensional imaging. For example, presently available commercial catheter-based intracardiac probes used for clinical ultrasound B-scan imaging suffer from limitations associated with the monoplanar nature of the B-scan images.

A typical probe, such as an ultrasound probe, typically includes a transducer package, a multi-wire cable connecting the transducer to the rest of an imaging system, such as an ultrasound system, and other miscellaneous mechanical hardware such as the probe housing, thermal and/or acoustic potting material and electrical shielding. However, the high density of interconnections required to address each transducer element in a two-dimensional transducer array disadvantageously results in poor space efficiency of the transducer assemblies.

Previously available methods of fabricating transducer arrays have incorporated multi-layer flexible interconnect circuits to facilitate coupling the plurality of transducer elements. These multi-layer flex circuits route conductors on multiple flexible layers parallel to the plane of the transducer elements. However, such interconnect circuits are expensive and fail to efficiently utilize space within a catheter. Additionally, acoustic performance of transducers fabricated with such methods has suffered due to the presence of an acoustically unfavorable interconnect circuit immediately underneath the active elements. Disadvantageously, many previous attempts to facilitate space efficient interconnections of transducer elements have had limited effect on imaging performance of the catheters.

There is therefore a need for a transducer assembly capable of real-time three-dimensional imaging for use in a probe employed in space critical applications such as intracardiac imaging. In particular there is a significant need for a design of a transducer assembly that advantageously enhances the imaging performance of a probe while maximizing the aperture. Also, it would be desirable to develop a simple and cost-effective method of fabricating a transducer assembly capable of real-time three-dimensional imaging.

BRIEF DESCRIPTION

Briefly, in accordance with aspects of the present technique, a composite structure of a z-axis interconnect is presented. The composite structure includes a plurality of layers of backing material alternatingly arranged between a plurality of interconnect layers, where the plurality of interconnect layers is configured to facilitate coupling the composite structure of the z-axis interconnect to a transducer array, where the composite structure of z-axis interconnect is configured for use in an invasive probe.

In accordance with another aspect of the present technique, a transducer assembly is presented. The assembly includes a composite structure of a z-axis interconnect. In addition, the assembly includes a transducer array disposed proximate the composite structure of the z-axis interconnect, where the transducer array comprises one or more transducer elements disposed in a array, and where the transducer array is in operative association with the composite structure of the z-axis interconnect, where the transducer assembly is configured for use in an invasive probe.

In accordance with yet another aspect of the present technique, a method of forming a composite structure of a z-axis interconnect is presented. The method includes alternatingly disposing a plurality of layers of backing material between a plurality of interconnect layers to form the composite structure of a z-axis interconnect having a first end and a second end, where the first end is configured to facilitate coupling the composite structure to a transducer array having one or more transducer elements and the second end is configured to facilitate coupling the composite structure to a cable assembly or electronics, where the composite structure of z-axis interconnect is configured for use in an invasive probe.

In accordance with further aspects of the present technique, a method for forming a transducer assembly is presented. The method includes alternatingly disposing the plurality of layers of backing material between a plurality of interconnect layers to form a composite structure of a z-axis interconnect having a first end and a second end, where the first end is configured to facilitate coupling the composite structure to a transducer array and the second end is configured to facilitate coupling the composite structure to a cable assembly or electronics. Furthermore, the method includes coupling a transducer array having one or more transducer elements arranged in a spaced relationship to the composite structure of the z-axis interconnect, where the transducer array and the composite structure are in operative association, where the transducer assembly is configured for use in an invasive probe.

In accordance with yet another aspect of the present technique, a system is presented. The system includes an acquisition subsystem configured to acquire image data, where the acquisition subsystem comprises an invasive probe configured to image a region of interest, where the invasive probe comprises at least one transducer assembly, where the at least one transducer assembly comprises a composite structure of a z-axis interconnect and a transducer array, where the composite structure of the z-axis interconnect comprises a plurality of layers of backing material alternatingly arranged between a plurality of interconnect layers, and where the plurality of interconnect layers is configured to facilitate coupling the composite structure of the z-axis interconnect to the transducer array. Moreover, the system also includes a processing subsystem in operative association with the acquisition subsystem and configured to process the image data acquired via the acquisition subsystem.

DRAWINGS

These and other features, aspects, and advantages of the present invention will become better understood when the following detailed description is read with reference to the accompanying drawings in which like characters represent like parts throughout the drawings, wherein.

Figure 21:
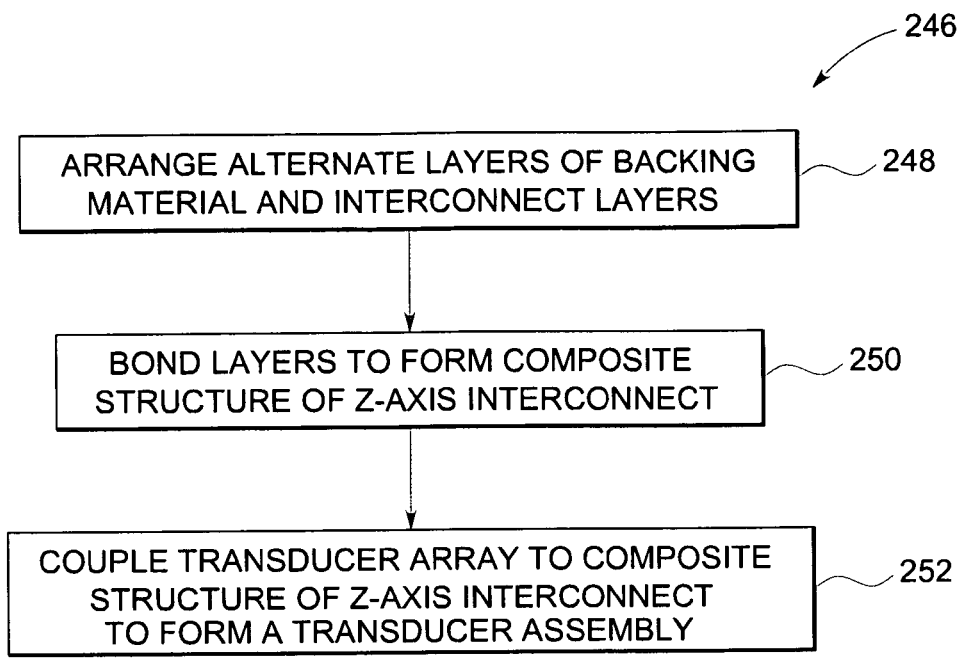
Figure 22:
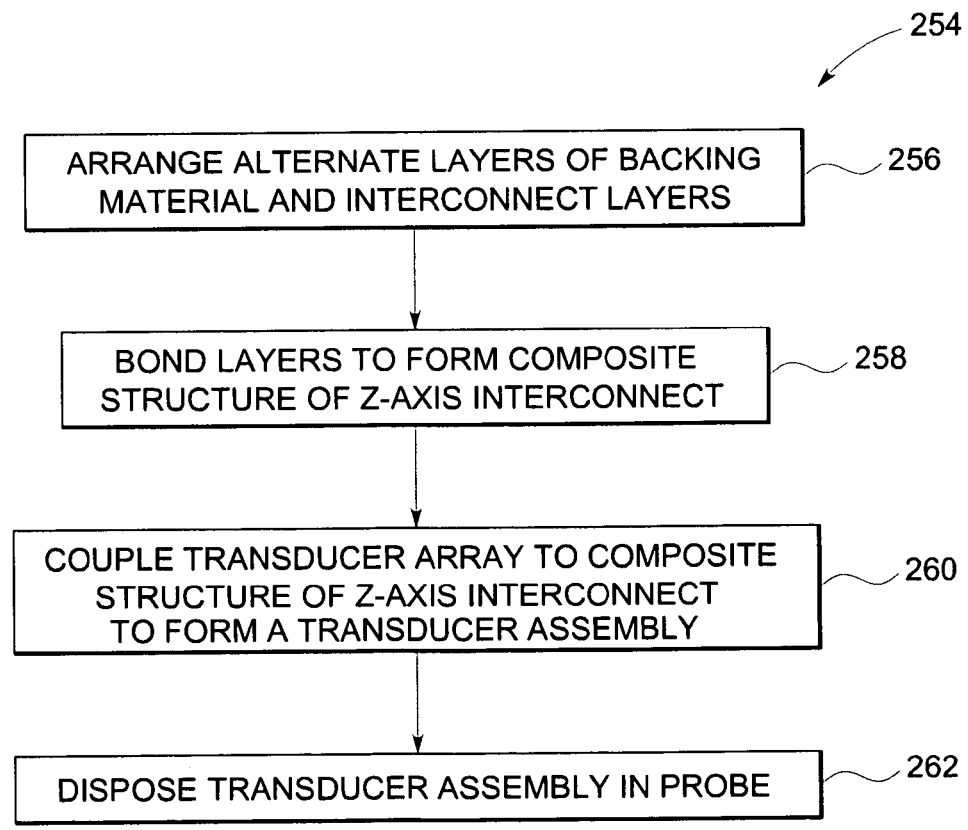

FIG. 21 is a flow chart depicting an exemplary method for forming a transducer assembly including the composite structure of z-axis interconnect, in accordance with aspects of the present technique; and FIG. 22 is a flow chart depicting an exemplary method for forming a probe including a transducer assembly having the composite structure of z-axis interconnect, in accordance with aspects of the present technique.

DETAILED DESCRIPTION

As will be described in detail hereinafter, a transducer assembly capable of real-time three-dimensional imaging for use in an invasive probe employed in space critical applications such as intracardiac imaging and methods of forming a transducer assembly are presented. It may be noted that, in one embodiment, the transducer array may include a two-dimensional transducer array. It is desirable to develop a transducer assembly that advantageously enhances the imaging performance of a probe, such as an invasive probe, while maximizing the aperture. Furthermore, it would be advantageous to enhance imaging performance of the probe by allowing a majority of area underneath a transducer element to be occupied by acoustic backing. Also, it would be desirable to develop a simple and cost-effective method of fabricating a transducer assembly capable of real-time three-dimensional imaging. The techniques discussed herein address some or all of these issues.

Figure 1:
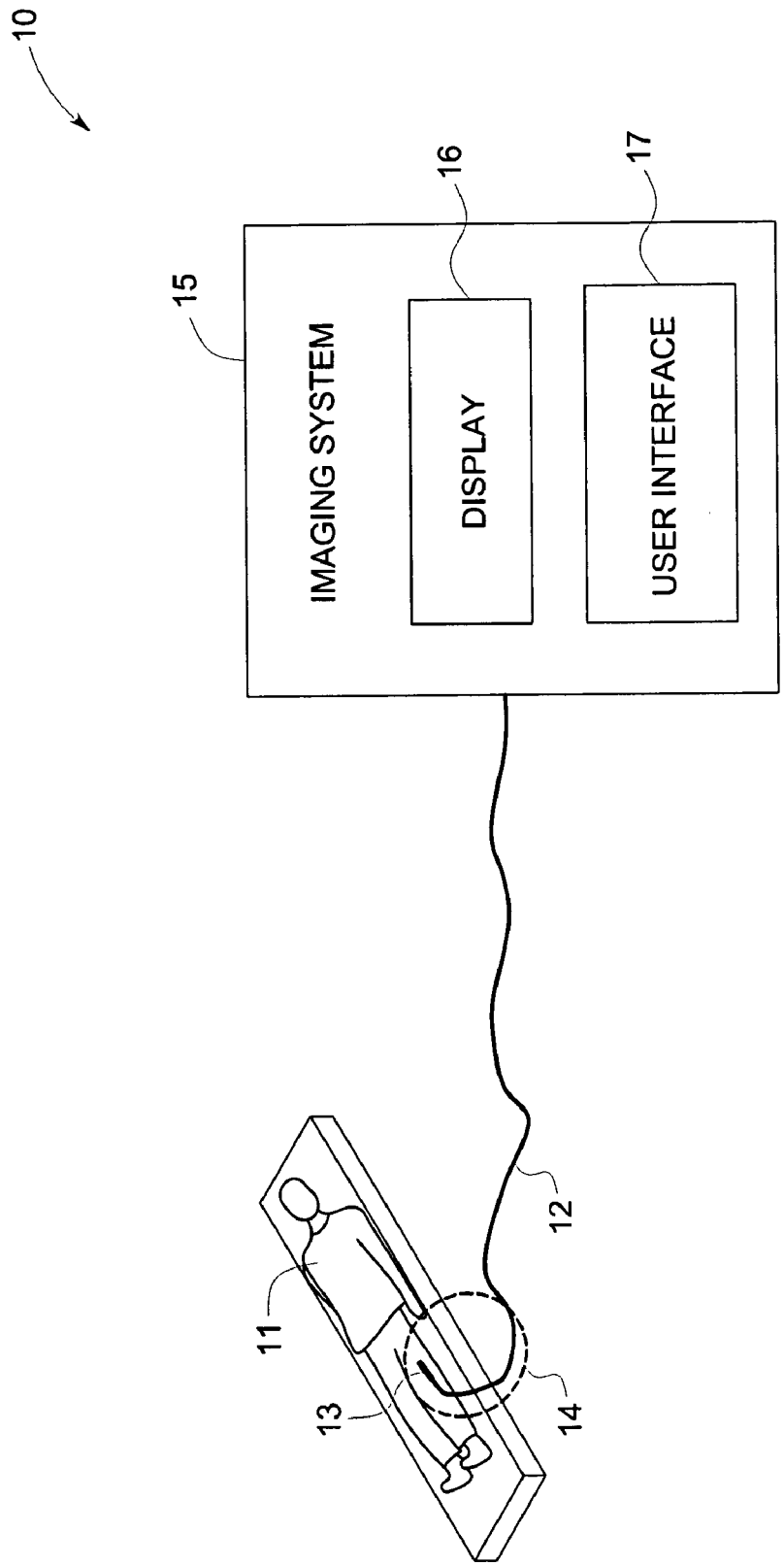
FIG. 1 is a block diagram of an exemplary probe-based imaging system, in accordance with aspects of the present technique.

FIG. 1 is a block diagram of an exemplary system 10 for use in imaging, in accordance with aspects of the present technique. The system 10 may be configured to facilitate acquisition of image data from a patient 11 via a probe 12. In other words, the probe 12 may be configured to acquire image data representative of a region of interest in the patient 11, for example. In accordance with aspects of the present technique, the probe 12 may be configured to facilitate interventional procedures. In other words, in a presently contemplated configuration the probe 12 may include an invasive probe. It should also be noted that, although the embodiments illustrated are described in the context of a catheter-based probe, other types of probes such as endoscopes, laparoscopes, surgical probes, transrectal probes, transvaginal probes, intracavity probes, probes adapted for interventional procedures, or combinations thereof are also contemplated in conjunction with the present technique. Reference numeral 13 is representative of a portion of the probe 12 disposed inside the patient 11.

In certain embodiments, the probe may include an imaging catheter-based probe 12. Further, an imaging orientation of the imaging catheter 12 may include a forward viewing catheter, a side viewing catheter, or an oblique viewing catheter. However, a combination of forward viewing, side viewing and oblique viewing catheters may also be employed as the imaging catheter 12. The imaging catheter 12 may include a real-time imaging transducer assembly (not shown).

The system 10 may also include an imaging system 15 that is in operative association with the imaging catheter 12 and configured to facilitate acquisition of image data. It should be noted that although the exemplary embodiments illustrated hereinafter are described in the context of a medical imaging system, such as an ultrasound system, other imaging systems such as, but not limited to, optical imaging systems, pipeline inspection systems, liquid reactor inspection systems, or other imaging systems are also contemplated.

Further, the imaging system 15 may be configured to display an image representative of a current position of the imaging catheter 12 within a region of interest in the patient 11. As illustrated in FIG. 1, the imaging system 15 may include a display area 16 and a user interface area 17. In accordance with aspects of the present technique, the display area 16 of the imaging system 15 may be configured to display the image generated by the imaging system 15 based on the image data acquired via the imaging catheter 12. Additionally, the display area 16 may be configured to aid the user in visualizing the generated image. Also, reference numeral 14 is representative of portion of the imaging catheter 12.

Figure 2:
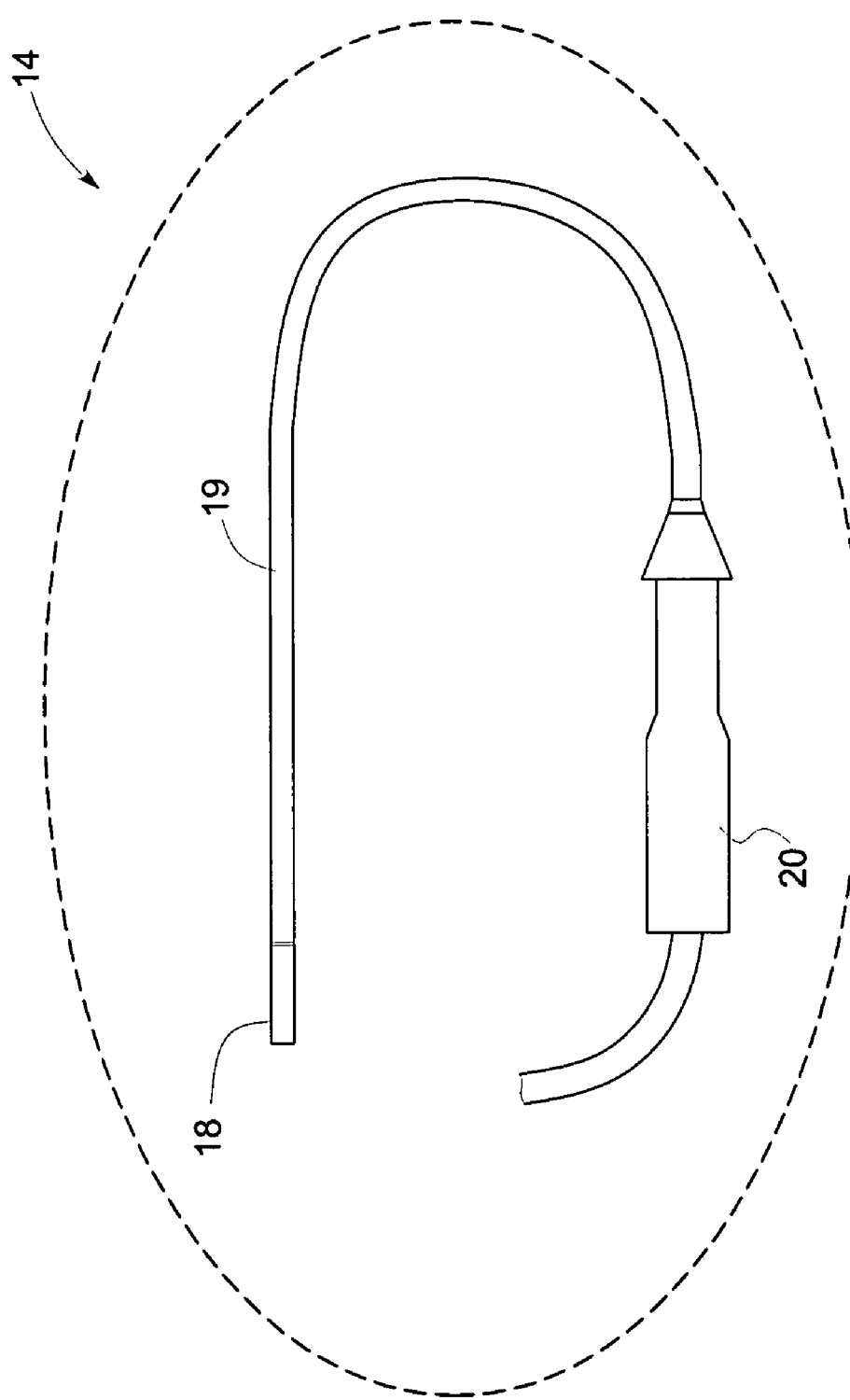
FIG. 2 illustrates a portion of an invasive probe including an exemplary transducer assembly for use in the system illustrated in FIG. 1, in accordance with aspects of the present technique.

FIG. 2 illustrates an enlarged view of the portion 14 of the imaging catheter 12. As depicted in FIG. 2, a transducer assembly 18 configured for use in an invasive probe may be disposed on a distal end of a shaft 19. The imaging catheter 12 may also include a handle 20 configured to facilitate a user to manipulate the shaft 19. A distance between the transducer assembly 18 and the handle 20 may be in a range from about 10 cm to about 150 cm depending on the type of probe and application.

Figure 3:
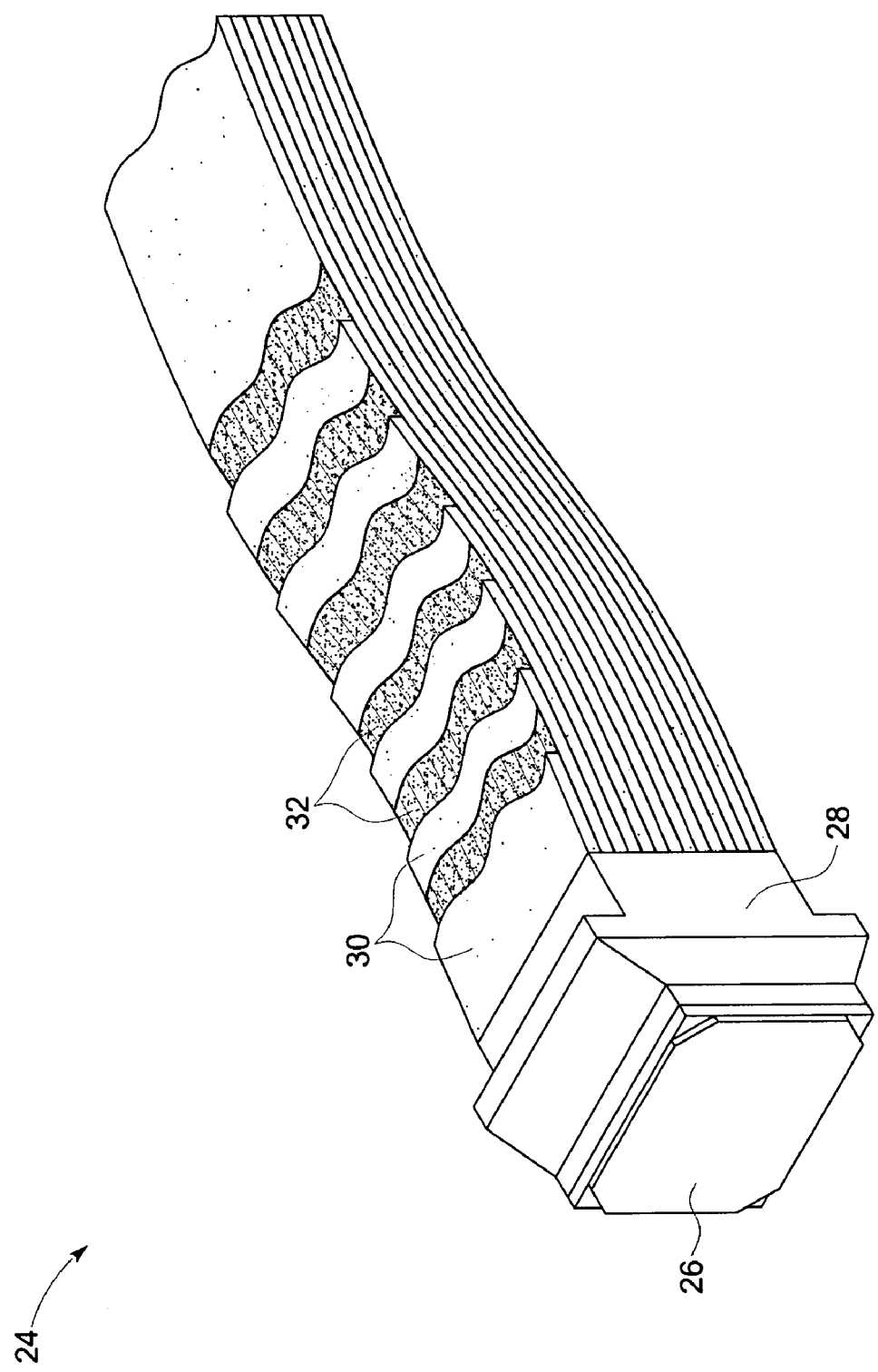
FIG. 3 is a perspective view of a transducer assembly for use in the system illustrated in FIG. 1, in accordance with aspects of the present technique.

Turning now to FIG. 3, a perspective side view of a transducer assembly 24 for use in the system 10 depicted in FIG. 1 is illustrated. Typically, the transducer assembly 24, for example, an acoustic transducer assembly, as illustrated in FIG. 2, may include one or more transducer elements (not shown), one or more matching layers (not shown) and a lens (not shown). The transducer elements may be arranged in a spaced relationship, such as, but not limited to, an array of transducer elements disposed on a layer, where each of the transducer elements may include a transducer front face 26 and a transducer rear face (not shown). As will be appreciated by one skilled in the art, the transducer elements may be fabricated employing materials, such as, but not limited to lead zirconate titanate (PZT), polyvinylidene difluoride (PVDF), composite PZT, or micromachined silicon. The transducer assembly 24 may also include one or more matching layers disposed adjacent to the front face 26 of the array of transducer elements, where each of the matching layers may include a matching layer front face and a matching layer rear face. The matching layers facilitate matching of an impedance differential that may exist between the high impedance transducer elements and a low impedance patient or subject 11 (see FIG. 1). The lens may be disposed adjacent to the matching layer front face and provides an interface between the patient and the matching layer. Additionally, in certain embodiments, the lens may be configured to facilitate focusing of the ultrasound beam. Alternatively, the lens may include a non-focusing layer.

In addition, the transducer assembly 24 may include a backing structure 28, having a front face and a rear face, which may be fabricated employing a suitable acoustic damping material possessing high acoustic losses. The backing structure 28 may be acoustically coupled to the rear face of the array of transducer elements, where the backing structure 28 facilitates the attenuation of acoustic energy that may emerge from the rear face of the array of transducer elements.

As previously discussed, it may be desirable to enhance the imaging performance of a probe in space critical situations while maximizing the aperture. More particularly, it may be desirable to develop a transducer assembly with interconnections that facilitate space efficiency and improved performance. Accordingly, in a presently contemplated configuration, the backing structure 28 may include an exemplary composite structure of z-axis interconnect where a plurality of layers of backing material 30 are alternatingly disposed between a plurality of layers of interconnect 32. The exemplary transducer assembly 24 having the z-axis interconnect will be described in greater detail hereinafter.

Moreover, the transducer assembly 24 may also include an electrical shield (not shown) that facilitates the isolation of the transducer elements from the external environment. The electrical shield may include metal foils, where the metal foils may be fabricated employing metals such as, but not limited to, copper, aluminum, brass, and gold.

Figure 4:
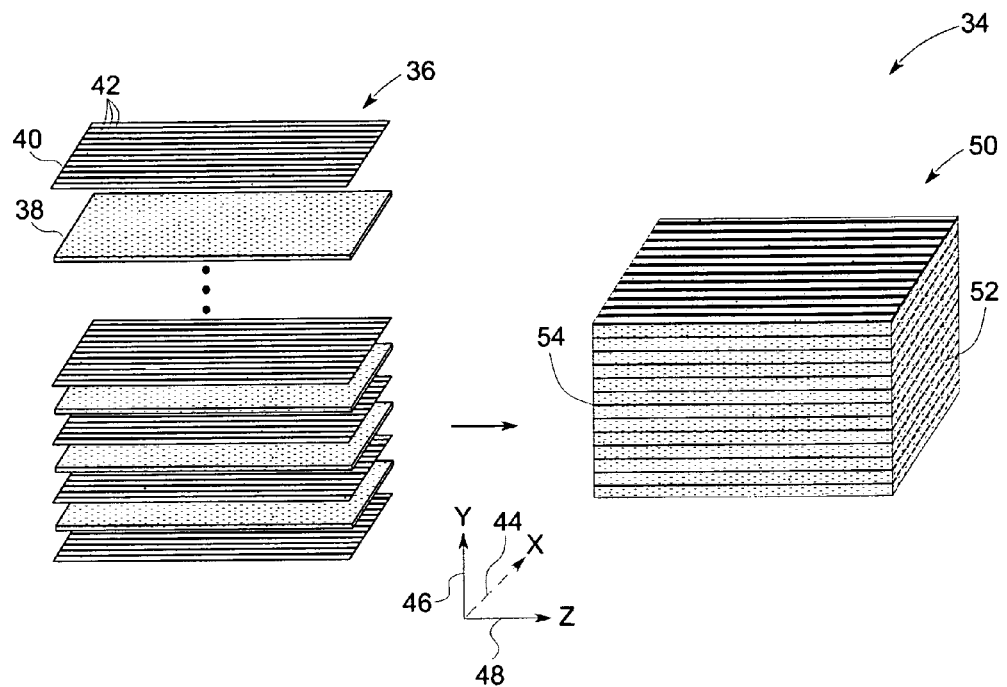
FIG. 4 is an exploded view of an exemplary embodiment of a composite structure of z-axis interconnect for use in a transducer assembly, in accordance with aspects of the present technique.

As mentioned hereinabove, the transducer assembly 24 (see FIG. 3) includes an exemplary z-axis interconnect. FIG. 4 illustrates assembly 34 of an exemplary embodiment of a z-axis interconnect. Reference numeral 36 represents an exploded view of the z-axis interconnect. In a presently contemplated configuration, the z-axis interconnect includes an arrangement where a plurality of layers of backing material 38 are alternatively stacked with a plurality of interconnect layers 40. Each of the plurality of interconnect layers 40 may include at least one conductive element 42 patterned thereon and may be configured to facilitate coupling the z-axis interconnect to a transducer array. It may be noted that the plurality of layers of backing material may be configured to serve a structural function and/or an acoustic function. In one embodiment, the layers of backing material may be configured to provide support to a transducer array that may be built thereon. In certain other embodiments, the layers of backing material may be configured to facilitate attenuation of acoustic energy that may emerge from an array of transducer elements. However, if the transducer array includes a dematching layer, the backing layer may be configured to facilitate only supporting the transducer array. In the illustrated embodiment of FIG. 4, X, Y and Z directions are represented by reference numerals 44, 46 and 48 respectively. Furthermore, as depicted in FIG. 4, the plurality of interconnect layers 40 may be alternatively stacked with plurality of layers of backing material 38 in the Y-direction 46.

Moreover, a stack formed by alternatingly arranging the plurality of interconnect layers 40 with plurality of layers of backing material 38 may be bonded to form a composite structure 50 of z-axis interconnect having a first end 52 and a second end 54. The first end 52 of the composite structure 50 may be configured to facilitate coupling the composite structure 50 to a transducer array (not shown) having one or more transducer elements (not shown). In addition, the second end 54 of the composite structure 50 may be configured to facilitate operatively coupling the composite structure 50 to a cable assembly or electronics (not shown), for example. In certain embodiments, the electronics may include a circuit board, an integrated circuit die or an integrated circuit package. This composite structure 50 may be configured such that a thickness of each of the plurality of layers of backing material 38 may be relatively greater than a thickness of each of the plurality of the interconnect layers 40. For example, the thickness of each of the plurality of layers of backing material 38 may be in a range from about 50 μm to about 300 μm, while the thickness of each of the plurality of interconnect layers 40 may be in a range from about 25 μm to about 125 μm. It may be noted that the respective values of the thickness of the layers of backing material and thickness of the interconnect layers may be dependent on a desired inter-element pitch of the transducer array, which is dependent on the frequency of operation of the transducer. By implementing a transducer assembly having the composite structure 50 as described hereinabove, acoustic performance of the transducer assembly may be advantageously enhanced.

In certain embodiments, each of the plurality of interconnect layers 40 may include a flexible interconnect layer. The flexible interconnect layer may include at least one conductive element patterned on a flexible substrate having a top side and a bottom side, where the at least one conductive element may be configured to facilitate coupling the composite structure 50 to a respective transducer element on a transducer array. In one embodiment, the flexible interconnect layer may include at least one metal trace patterned on a dielectric film.

With returning reference to the composite structure of z-axis interconnect 50, in accordance with aspects of the present technique, a pitch of the conductive elements on the first end 52 may be different from a pitch of the conductive elements on the second end 54. In other words, the pitch of the conductive elements on the first end 52 and the second end 54 may be configured to match a pitch of a respective device to which the composite structure 50 may be coupled. For example, as previously noted, the first end 52 of the composite structure 50 may be configured to facilitate coupling the composite structure 50 to a transducer array having one or more transducer elements. Accordingly, the pitch of the conductive elements on the first end 52 may be configured to match the pitch of the transducer elements on the transducer array. Furthermore, as previously noted, the second end 54 of the composite structure 50 may be configured to facilitate coupling the composite structure 50 to a cable assembly or electronics. The pitch of the conductive elements on the second end 54 may be configured to match a pitch of connecting elements on the cable assembly, for example.

Furthermore, it may be noted that a cross-sectional shape of the first end 52 of the composite structure 50 may be different from a cross-sectional shape of the second end 54 of the composite structure 50. Accordingly, the plurality of layers of backing material 38 and the plurality of interconnect layers 40 may be arranged to form a composite structure 50 having a predetermined shape, where the predetermined shape may include a square, a rectangle, an octagon, a circle, a rhombus, a triangle, or combinations thereof. In other words, a geometry of the composite structure of z-axis interconnect may be determined by a geometry of each of the plurality of layers of backing material 38 and the plurality of interconnect layers 40. It may also be noted in accordance with exemplary aspects of the present technique, a cross-sectional shape of the first end 52 may be different from the cross-sectional shape of the second end 54 of the composite structure 50. Alternatively, the composite structure 50 may be machined to a desired shape after assembly.

Figure 5:
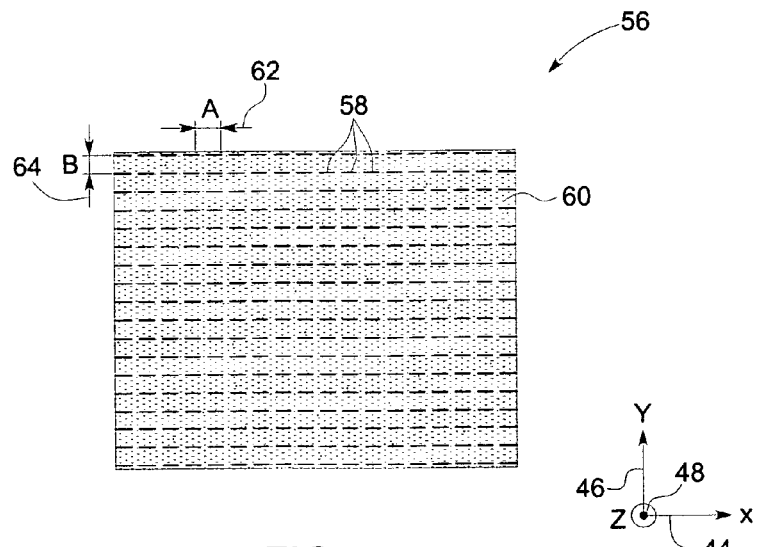
FIG. 5 is an end view of the composite structure of z-axis interconnect illustrated in FIG. 4, in accordance with aspects of the present technique.

FIG. 5 is an end view 56 of a composite structure of z-axis interconnect illustrated in FIG. 4, where the composite structure is shown as having a substantially rectangular cross-section. In other words, in the illustrated embodiment, the composite structure 56 is formed using the plurality of layers of backing material and the plurality of interconnect layers that have a substantially rectangular shape. Consequent to stacking these layers of substantially rectangular shape, a composite structure of z-axis interconnect having a substantially rectangular volume may be formed. Reference numeral 60 represents the plurality of layers of backing material. Conductive elements on a plurality of interconnect layers are represented by reference numeral 58.

Furthermore, a pitch of the conductive elements 58 may determine a distance "A" 62 between conductive elements 58 adjacently disposed in the X-direction 44. Similarly, a distance "B" 64 between conductive elements 58 adjacently disposed in the Y-direction 46 may be determined by the respective thickness of the backing layer and the interconnect layer. In other words, the respective thickness of each of the plurality of layers of backing material and each of the plurality of interconnect layers may be configured such that when the layers of backing material and the interconnect layers are stacked to form the composite structure 56, a vertical spacing of the conductive elements on a first end of the composite structure 56 may be configured to match a desired vertical spacing of the transducer elements on the transducer array. In a similar fashion, a horizontal spacing between conductive elements patterned on each of the interconnect layers may be configured to match a desired spacing between coupling elements on a cable assembly, for example.

Figure 6:
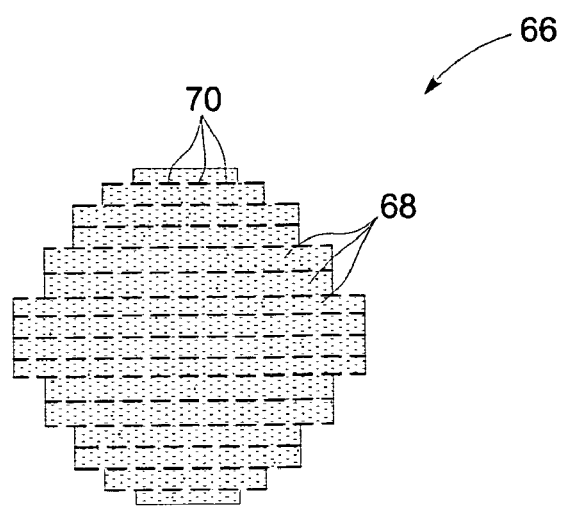
FIG. 6 is an end view of another exemplary embodiment of a composite structure of z-axis interconnect, in accordance with aspects of the present technique.

An end view 66 of a composite structure of z-axis interconnect having a substantially circular volume is illustrated in FIG. 6. The exemplary composite structure of z-axis interconnect having a substantially circular cross-section may be formed by stacking a plurality of layers of backing material and a plurality of interconnect layers such that layers have a progression of widths. For example, the layers of backing material and the plurality of interconnect layers disposed in the center of the z-axis interconnect may be relatively wider compared to outer layers of the interconnect structure. Reference numeral 68 represents a plurality of layers of backing material. Also, reference numeral 70 is representative of a plurality of conductive elements patterned on a plurality of interconnect layers (not shown).

Figure 7:
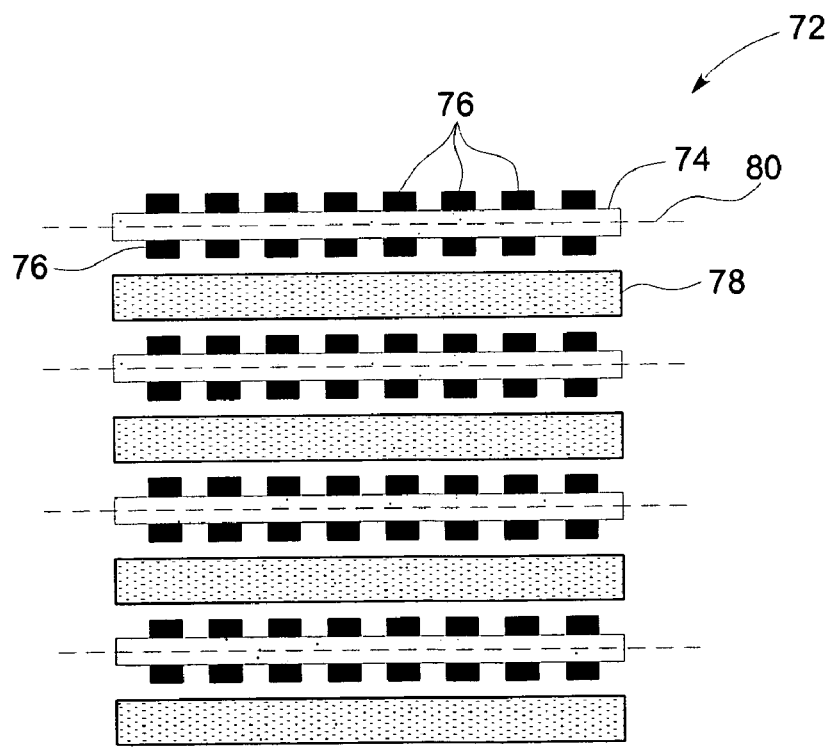
FIG. 7 is an exploded end view of yet another exemplary embodiment of a composite structure of z-axis interconnect, in accordance with aspects of the present technique.

Referring now to FIG. 7, an exploded end view 72 of another exemplary embodiment of z-axis interconnect is illustrated. In the illustrated embodiment, a plurality of double-sided interconnect layers 74 are alternatively stacked with a plurality of layers of backing material 78. Each of the plurality of double-sided interconnect layers 74 may be configured to include a plurality of conductive elements 76 disposed on a first side and a second side of a respective interconnect layer 74. By implementing the composite structure of z-axis interconnect 72 having a plurality of double-sided interconnect layers 74, only half the number of interconnect layers may be needed to facilitate coupling the composite structure 72 to a transducer array, thereby advantageously reducing the cost and complexity of a transducer assembly for use in space critical applications. Also, in the illustrated embodiment 72, a saw kerf 80 may pass through each of the plurality of double-sided interconnect layers 74. Employing this exemplary arrangement an amount of backing material disposed underneath the transducer may be advantageously maximized, thereby resulting in improved acoustic performance of the transducer.

In certain embodiments, a composite structure of z-axis interconnect may include a plurality of layers of backing material that are ground to a predetermined desirable thickness, where each of the plurality of layers of backing material has a respective top side and bottom side. A plurality of conductive elements may then be patterned directly on the top side of each of the plurality of layers of backing material, the bottom side of each of the plurality of layers of backing material or both. The plurality of these layers of backing material may then be stacked and bonded to form a composite structure of z-axis interconnect having the conductive traces disposed directly on the layer of backing material rather than on a separate carrier.

Figure 8:
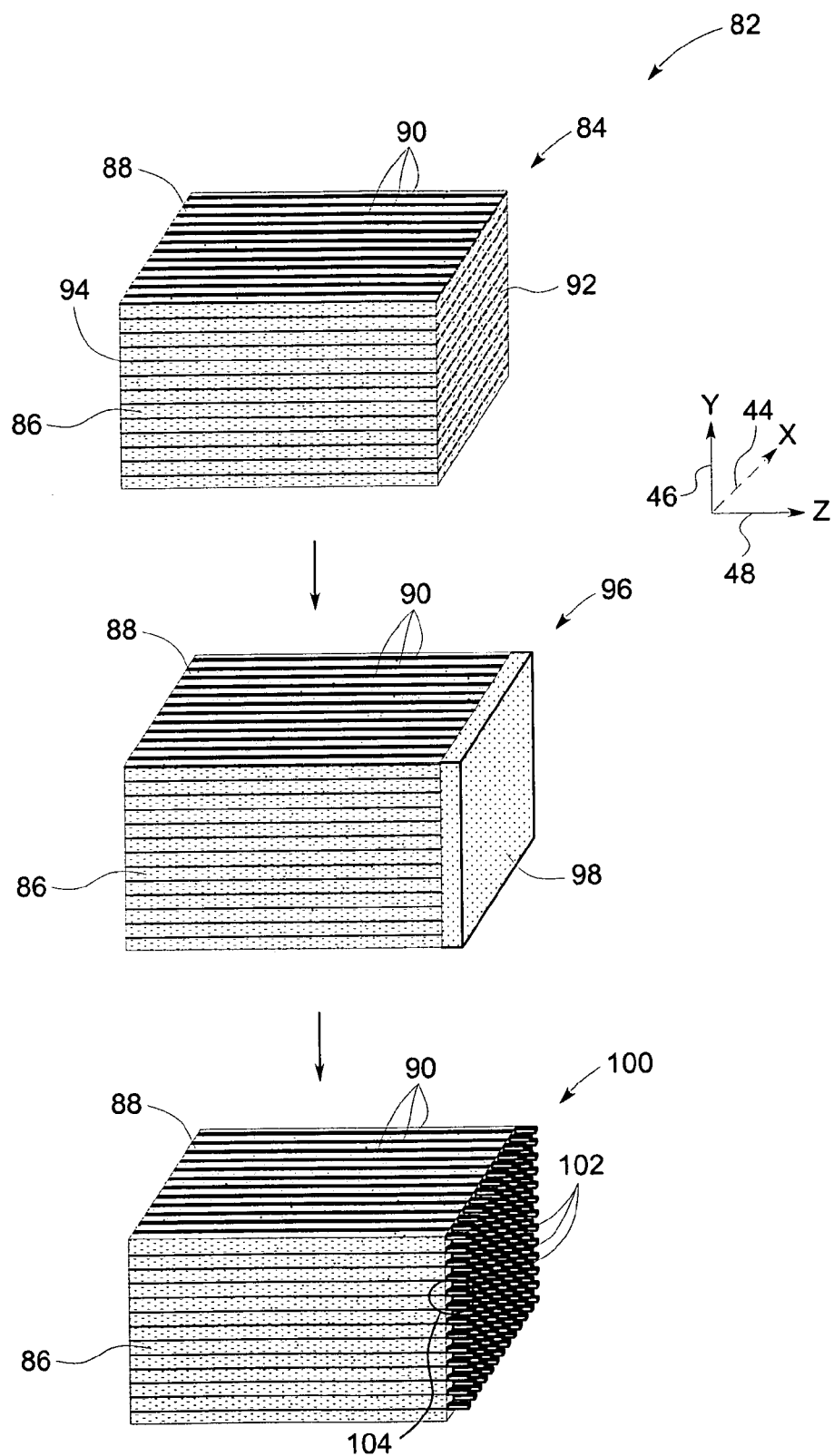
FIG. 8 is a diagram showing the assembly of an exemplary embodiment of a transducer assembly including a lead zirconate titanate (PZT) transducer array and the z-axis interconnect illustrated in FIG. 4, in accordance with aspects of the present technique.

FIG. 8 illustrates an exemplary method 82 for forming a transducer assembly, in accordance with aspects of the present technique. Reference numeral 84 is representative of a composite structure of z-axis interconnect. As previously described, the composite structure 84 may be formed by alternatingly arranging a plurality of layers of backing material 86 between a plurality of interconnect layers 88 Further, at least one conductive element 90 may be patterned on a respective interconnect layer 88 to facilitate coupling the composite structure 84 to a transducer array. The plurality of layers of backing material 86 and the plurality of interconnect layers 88 may then be bonded to form the composite structure of z-axis interconnect. Also, the composite structure 84 is shown as having a first end 92 configured to facilitate coupling the composite structure 84 to a transducer array and a second end 94 configured to facilitate coupling the composite structure 84 to a cable assembly, for example.

Following construction of the composite structure of z-axis interconnect 84, transducer material 98 may then be disposed adjacent the first end 92 of the composite structure 84. The transducer material 98 may then be fashioned into a transducer array, where the transducer array may include one or more transducer elements arranged in a spaced relationship, in one embodiment. According to aspects of the present technique, the transducer array may include a lead zirconate titanate (PZT) array or a micromachined ultrasound (MUT) array. The transducer array may be operatively coupled to the composite structure 84 to form a transducer assembly 100.

It should be noted that it may be desirable to grind and polish the first end 92 of the composite structure 84 prior to operatively coupling the composite structure 84 and the transducer material 98 to facilitate enhanced coupling to the one or more transducer elements of the transducer array. In the illustrated embodiment, the transducer material 98 may include PZT transducer material. Additionally, it may be advantageous to metalize the composite structure of z-axis interconnect 84 to facilitate improved electrical contact between the composite structure 84 and transducer array 98. Reference numeral 100 is representative of a transducer assembly where the PZT transducer material 98 may be sectioned or diced to form individual transducer elements 102. Furthermore, reference numeral 104 represents a portion of the diced transducer assembly having one or more transducer elements 102.

Figure 9:
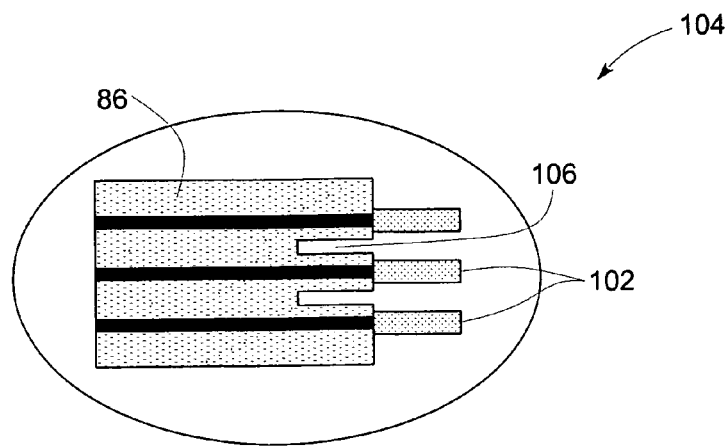
FIG. 9 is an enlarged view of a portion of the transducer assembly illustrated in FIG. 8.

FIG. 9 is an enlarged view of the portion 104 of the transducer assembly illustrated in FIG. 8. As depicted in FIG. 9, in one embodiment, a plurality of saw kerfs 106 may extend into the plurality of layers of backing material 86 to facilitate isolation of the individual transducer elements 102.

Figure 10:
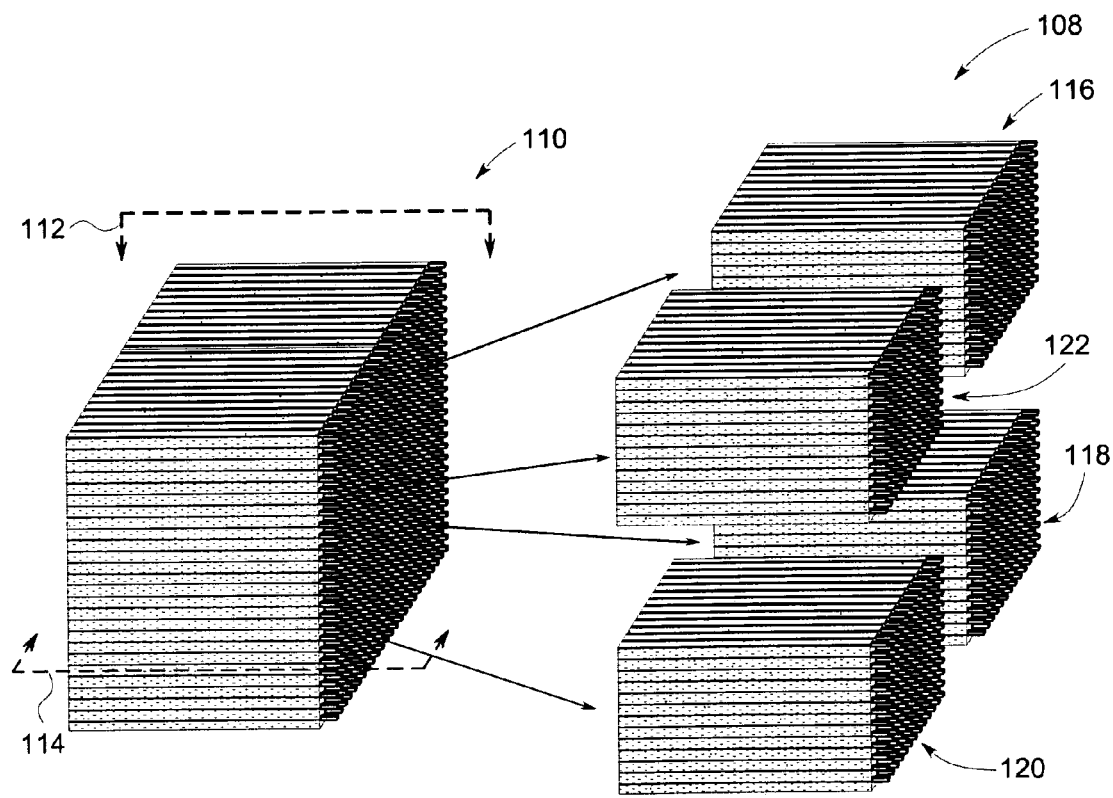
FIG. 10 is an exploded view of a plurality of transducer assemblies with the z-axis interconnect illustrated in FIG. 4, in accordance with aspects of the present technique.

Turning now to FIG. 10, a method 108 of forming a plurality of transducer assemblies having respective composite structures of z-axis interconnect is illustrated. As depicted in FIG. 10 a single transducer assembly 110 having a composite structure of z-axis interconnect may be diced along one or more directions to form a plurality of composite structures. In the illustrated embodiment, the single composite structure 110 may be diced along a first direction 112 and a second direction 114 to form four transducer assemblies 116, 118, 120 and 122. This method of forming a plurality of transducer assemblies from a single transducer assembly 110 advantageously provides a simple and cost-effective method of mass fabrication of a plurality of transducer assemblies having z-axis interconnect.

Figure 11:
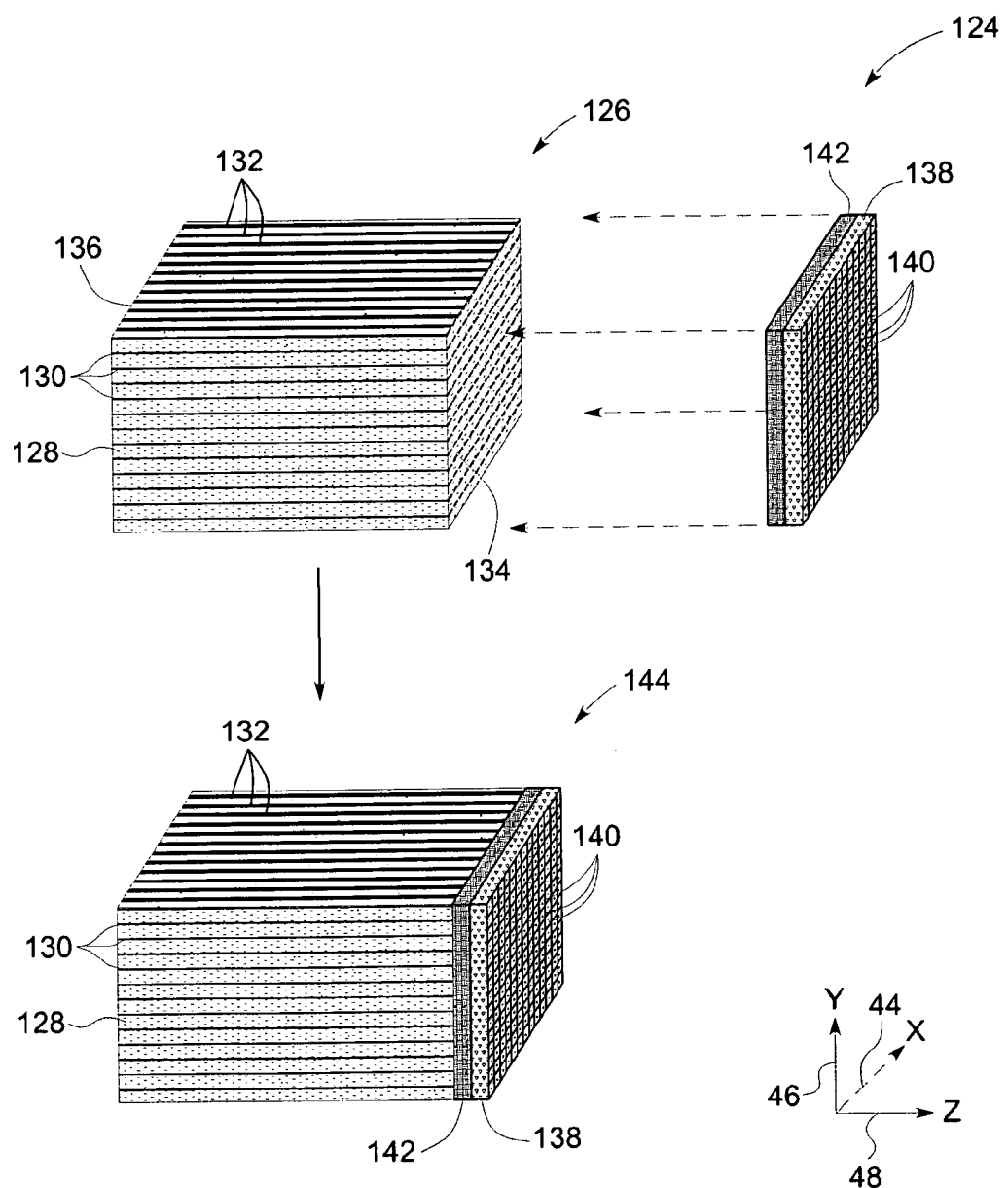
FIG. 11 is a diagram showing assembly of an exemplary embodiment of a transducer assembly including a micromachined ultrasound transducer (MUT) array and the z-axis interconnect illustrated in FIG. 4, in accordance with aspects of the present technique.

Referring now to FIG. 11, an exemplary method 124 for forming a transducer assembly having a composite structure of z-axis interconnect and a MUT transducer array is illustrated. Reference numeral 126 is representative of a composite structure of z-axis interconnect. As previously described, the composite structure 126 may be formed by alternatingly arranging a plurality of layers of backing material 128 between a plurality of interconnect layers 130. Further, each of the plurality of interconnect layers 130 may include at least one conductive element 132 patterned thereon, where the at least one conductive element 132 may be configured to facilitate coupling the composite structure 126 to a transducer array. Also, the composite structure 126 is shown as having a first end 134 configured to facilitate coupling the composite structure 126 to a transducer array and a second end 136 configured to facilitate coupling the composite structure 126 to a cable assembly, for example.

As previously noted with reference to FIG. 8, following construction of the composite structure of z-axis interconnect 126, a transducer array 138 may then be disposed adjacent the first end 134 of the composite structure 126. In one embodiment, one or more transducer elements 140 may be arranged in a spaced relationship to form a transducer array 138. The MUT transducer array 138 may include one or more layers of electronics 142 disposed proximate the transducer array, where the one or more layers of electronics 142 may be configured to facilitate coupling the transducer elements 140 to the composite structure of z-axis interconnect 126. Alternatively, MUT transducer arrays 138 fabricated with silicon processing methods may include through wafer vias (not shown) to facilitate coupling the transducer elements 140 to the conductive traces 132 on the composite structure of z-axis interconnect 126. Furthermore, the MUT transducer array 138 may be operatively coupled to the composite structure 126 to form a transducer assembly 144. It may be noted that it may be desirable to grind and polish the first end 134 of the composite structure 126 prior to operatively coupling the composite structure 126 and the transducer array 138 to enhance electrical coupling. Additionally, it may be advantageous to metalize the composite structure of z-axis interconnect 126 to facilitate improvement of electrical contact between the composite structure 126 and transducer array 138.

It should be noted that the transducer assembly thus formed may include one of a forward viewing transducer assembly for use in a forward viewing probe, a side viewing transducer assembly for use in a side viewing probe, or an oblique viewing transducer assembly for use in an oblique viewing probe, and will be described in greater detail with reference to FIGS. 14-20.

Figure 12:
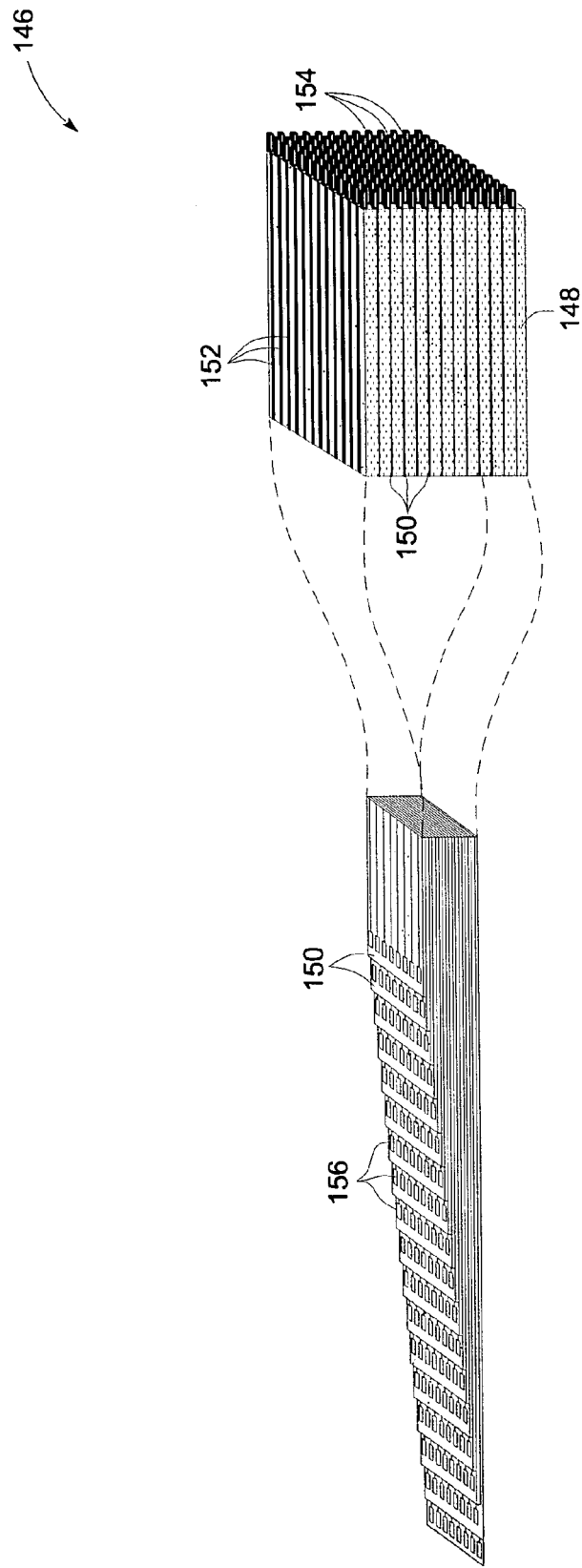
FIG. 12 is a perspective view of staggered termination of interconnect of the transducer assembly, in accordance with aspects of the present technique.

FIG. 12 is a perspective view 146 of an exemplary staggered termination of interconnect of a transducer assembly, in accordance with aspects of the present technique. As depicted in FIG. 12, a transducer assembly 146 having a composite structure of z-axis interconnect may be formed as previously described with reference to FIG. 8. Reference numeral 148 is representative of a plurality of layers of backing material. Also, reference numeral 150 represents a plurality of interconnect layers and reference numeral 152 is representative of at least one conductive element patterned on the interconnect layer 150. A plurality of transducer elements is represented by reference numeral 154. In a presently contemplated configuration, the plurality of interconnect layers 150 may be configured to have staggered lengths. The staggered lengths of the plurality of interconnect layers 150 advantageously facilitate exposure of all of conductive elements 152 via solder pads 156 thereby allowing relatively easy termination of associated cabling.

Figure 13:
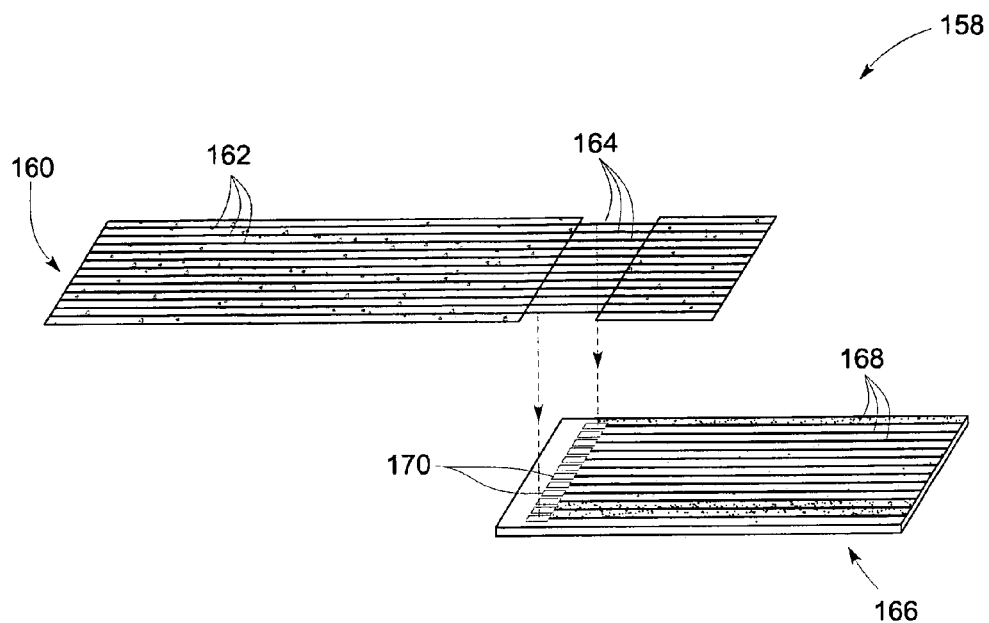
FIG. 13 is a perspective view of mass termination of probe cabling onto the z-axis interconnect, in accordance with aspects of the present technique.

Mass termination 158 of associated cabling, such as cabling associated with a probe, onto an individual interconnect layer 166 is illustrated in FIG. 13. A probe cable 160 is illustrated as having at least one conductive element 162. In one embodiment, the probe cable 160 may be a ribbon cable. Further, the probe cable 160 may have exposed conductive elements 164 to facilitate easy termination on the individual interconnect layer 166 of a composite structure of z-axis interconnect. Also, the interconnect layer 166 may have at least one conductive element 168 patterned thereon. Additionally, the interconnect layer 166 may have at least one solder pad 170 disposed on a proximal end of the interconnect layer 166. These solder pads 170 may be arranged on the interconnect layer 166 to match a spacing between the conductive elements 164 on the probe cable 160. Mass termination techniques such as hot bar bonding may then be employed to couple the probe cable 160 to the interconnect layer 166.

Figure 14:
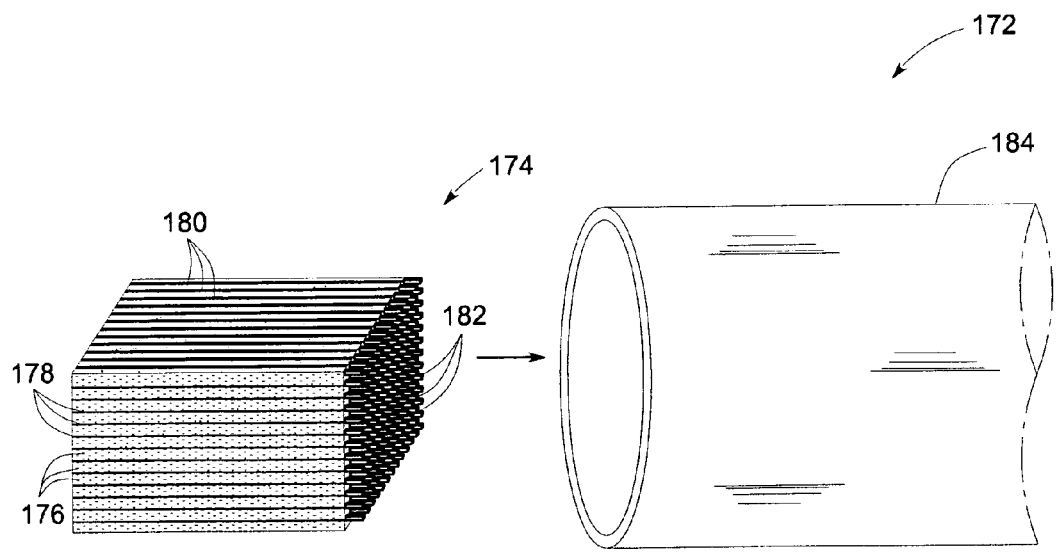
FIG. 14 is a diagram showing assembly of an exemplary embodiment of an invasive probe including the transducer assembly illustrated in FIG. 8, in accordance with aspects of the present technique.

FIG. 14 illustrates a method 172 of forming an invasive probe having a composite structure of z-axis interconnect. In certain embodiments, the invasive probe may include an imaging catheter, an endoscope, a laparoscope, a surgical probe, an intracavity probe, or a probe adapted for interventional procedures, as previously noted. A transducer assembly 174 may be produced as previously described. A composite structure of z-axis interconnect may be formed by alternatingly stacking a plurality of layers of backing material 176 with a plurality of interconnect layers 178 where each of the plurality of interconnect layers 178 may have at least one conductive element 180 disposed thereon. Additionally, a transducer array having one or more transducer elements 182 may be operatively coupled to the composite structure of z-axis interconnect to form the transducer assembly 174. It should be noted that the transducer assembly 174 is representative of a forward viewing transducer assembly for use in a forward viewing probe 184. The transducer assembly 174 may then be disposed within the forward viewing probe 184.

Figure 15:
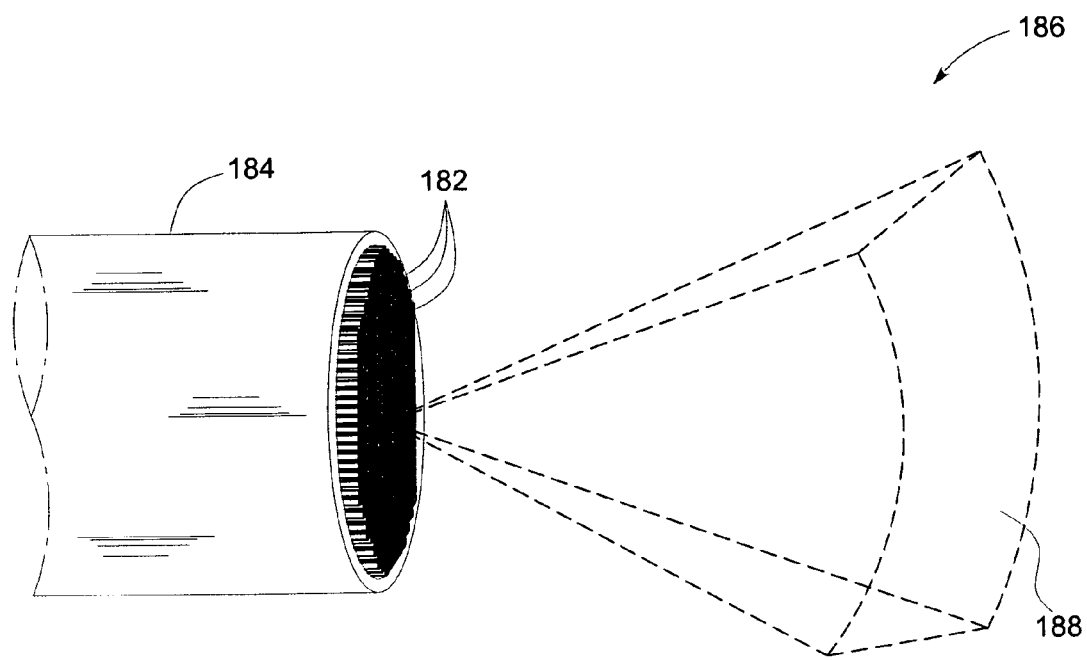
FIG. 15 is a perspective view of a forward viewing probe including the transducer assembly illustrated in FIG. 8, in accordance with aspects of the present technique.

In one embodiment, the forward viewing transducer assembly 174 may be disposed in a tip of the forward viewing probe 184 as illustrated in FIG. 15. FIG. 15 is a perspective view 186 of a forward viewing probe 184 including the transducer assembly having the composite structure of z-axis interconnect. Reference numeral 188 is representative of a forward viewing imaging volume of the forward viewing probe 184.

Figure 16:
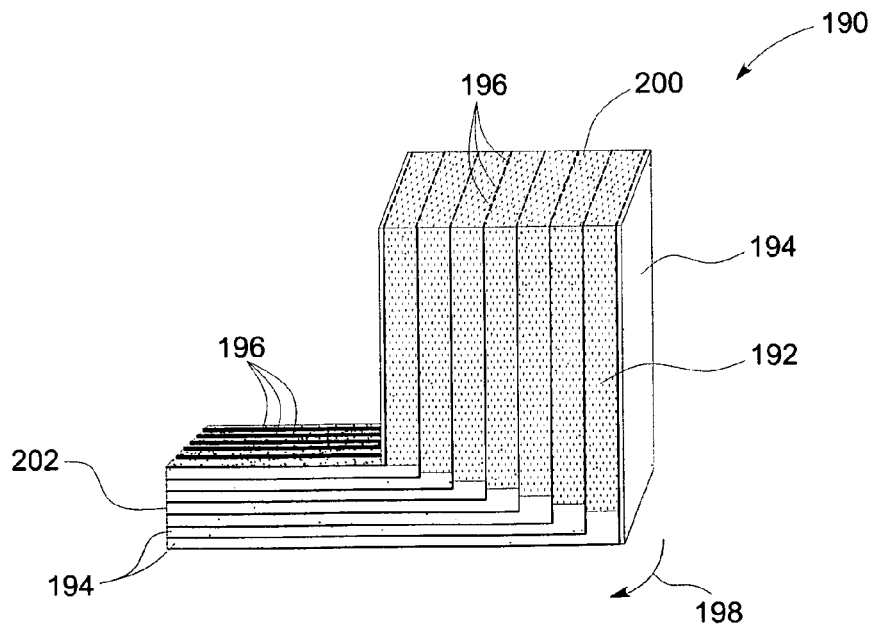
FIG. 16 is a perspective view of an exemplary embodiment of a composite structure for use in a side viewing probe, in accordance with aspects of the present technique.

Referring now to FIG. 16, a perspective view 190 of an exemplary embodiment of a composite structure of z-axis interconnect for use in a side viewing probe is illustrated. In certain embodiments, the composite structure of z-axis interconnect 190 may be fabricated employing methods used to fabricate composite structures of z-axis interconnect for use in forward viewing probes, with an additional step of bending interconnect layers to obtain a side viewing orientation. In other words, a plurality of layers of backing material 192 may be alternatingly stacked with a plurality of interconnect layers 194 and bonded to form a composite structure of z-axis interconnect, as previously described. Further, reference numeral 196 represents one or more conductive elements disposed on each of the plurality of interconnect layers 194. Each of the plurality of the interconnect layers 194 may then be bent in a direction 198 to form the composite structure of z-axis interconnect 190 having a side viewing orientation, where the side viewing composite structure 190 has a first end 200 and a second end 202. A transducer array (not shown) having one or more elements (not shown) may be operatively coupled to the first end 200 of the composite structure 190 to form a side viewing transducer assembly (not shown). In addition, the second end 202 of the composite structure 190 may be configured to facilitate operatively coupling the composite structure 190 to a cable assembly or electronics (not shown). In the illustrated embodiment of FIG. 16, each of the plurality of layers of backing material 192 may be configured to terminate at different lengths. However, in one embodiment, each of the plurality of layers of backing material 192 may be configured to terminate at substantially equal lengths.

In certain embodiments, each of the plurality of interconnect layers 194 may be bonded to a respective layer of backing material 192 to form a single interconnect-backing group (not shown). A plurality of such interconnect-backing groups may then be bonded to form the composite structure of z-axis interconnect.

Figure 17:
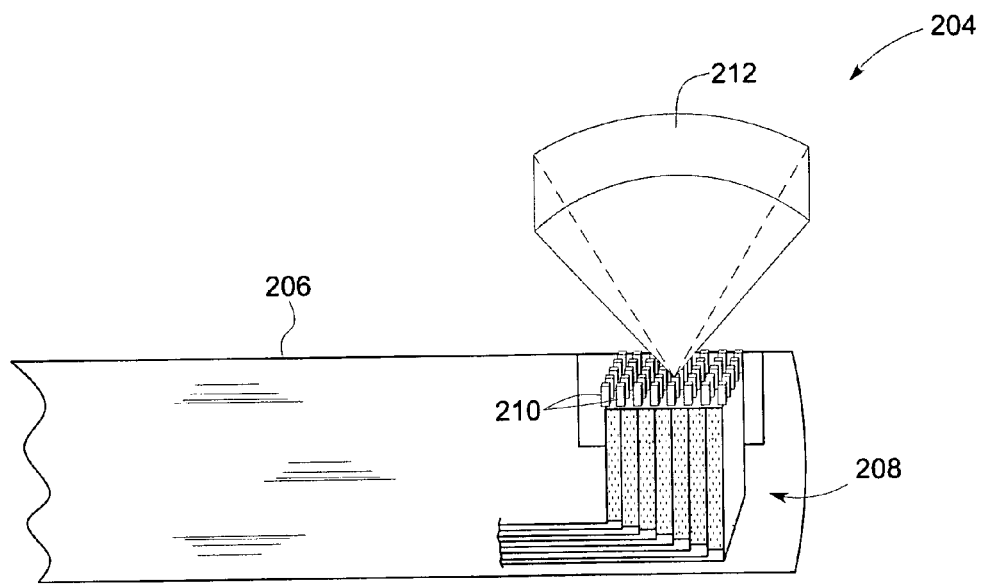
FIG. 17 is a perspective view of a side viewing probe including a side viewing transducer assembly, in accordance with aspects of the present technique.

Turning now to FIG. 17, a perspective view 204 of an exemplary side viewing probe including a side viewing transducer assembly 208 having the composite structure of z-axis interconnect is illustrated. The side viewing transducer assembly 208 is illustrated as having one or more transducer elements 210 disposed on a first end of the composite structure. As previously described with reference to FIGS. 14-15, the side viewing transducer assembly 208 may be disposed inside a side viewing probe 206. Reference numeral 212 is representative of a side viewing imaging volume of the side viewing probe 206.

Figure 18:
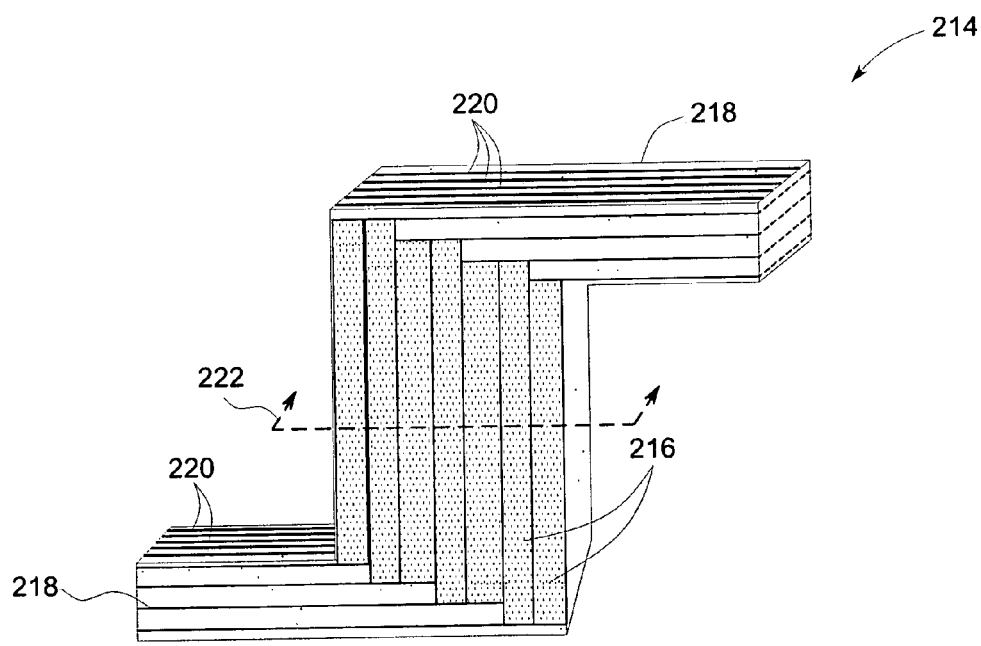
FIG. 18 is a perspective view of another exemplary embodiment of a transducer assembly for use in a side viewing probe, in accordance with aspects of the present technique.

FIG. 18 is a perspective view 214 of another exemplary embodiment of a transducer assembly for use in a side viewing probe. This exemplary embodiment of z-axis interconnect 214 may be formed by advantageously employing a relatively small number of interconnect layers to couple a composite structure of z-axis interconnect to the transducer elements arranged in rows and along columns on a transducer array (not shown). For example, in certain embodiments, the number of interconnect layers may be substantially equal to half the number of rows of transducer elements on the transducer array. Conductive elements 220 on interconnect layers 218 may be isolated by removing a substrate of the interconnect layers 218, for example. Backing material may then be woven between the isolated conductive elements 220 to distribute the conductive elements 220 over two or more rows of transducer elements.

A plurality of layers of backing material 216 and a plurality of interconnect layers 218 formed as described hereinabove may then be arranged to form a "S" shaped stack 214 as illustrated in FIG. 18. By implementing the composite structure of z-axis interconnect as illustrated in FIG. 18, a distance through the composite structure 214 may be configured to be substantially equal for all the conductive elements 220. Furthermore, ends of each of the plurality of interconnect layers 218 may be advantageously aligned. Tooling pins may be employed to align and hold the interconnect layers 218 during assembly. Additionally, the "S" shaped composite structure 214 may be cut along a direction 222 to form a plurality of composite structures of z-axis interconnect. As described hereinabove, respective first ends of composite structures may be ground and polished. In addition, transducer arrays may be coupled to the respective first ends of the composite structures to form respective side viewing transducer assemblies.

Figure 19:
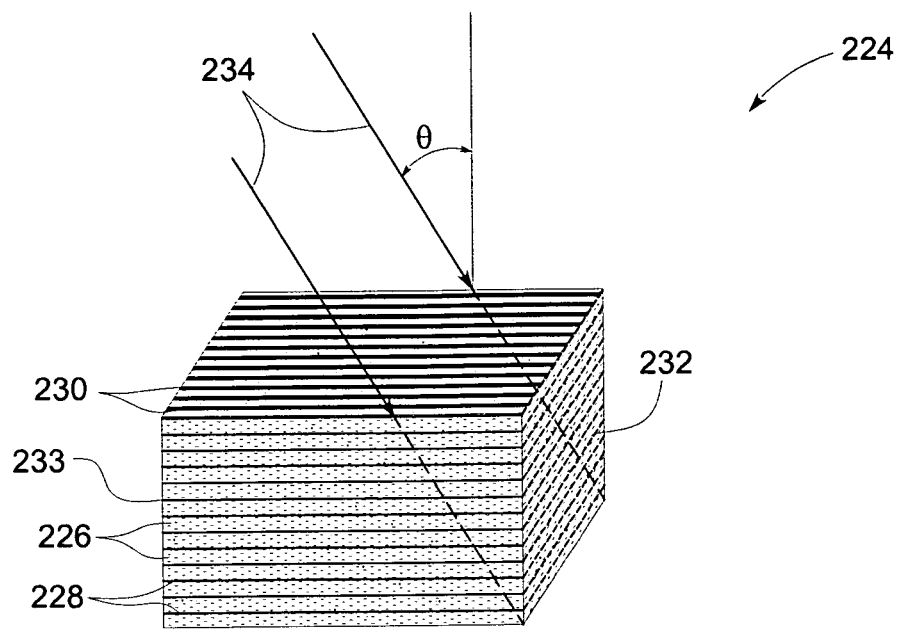
FIG. 19 is a perspective view of an exemplary embodiment of a composite structure of z-axis interconnect for use in an oblique viewing probe, in accordance with aspects of the present technique.

Referring now to FIG. 19, a perspective view 224 of an exemplary embodiment of a composite structure of z-axis interconnect for use in an oblique viewing probe is illustrated. In certain embodiments, the composite structure of z-axis interconnect 224 may be fabricated employing methods used to fabricate composite structures of z-axis interconnect for use in forward viewing probes, with an additional step of grinding a first end of the composite structure to obtain an oblique viewing orientation. In other words, a plurality of layers of backing material 226 may be alternatingly stacked with a plurality of interconnect layers 228 and bonded to form a composite structure of z-axis interconnect, as previously described. Further, reference numeral 230 is representative of a conductive element disposed on each of the plurality of interconnect layers 228. Also, a first end and a second end of the composite structure may be represented by reference numerals 232 and 233 respectively. The first end 232 of the composite structure 224 may be ground and polished at a predetermined oblique angle 234 to form a composite structure for use in an oblique viewing probe. In one embodiment, the oblique angle 234 may be in a range from about zero degrees to about sixty degrees. A transducer array (not shown) having one or more elements (not shown) may be operatively coupled to the first end 232 of the composite structure 224 to form an oblique viewing transducer assembly. In addition, the second end 233 of the composite structure 224 may be configured to facilitate operatively coupling the composite structure 224 to a cable assembly, for example (not shown).

Figure 20:
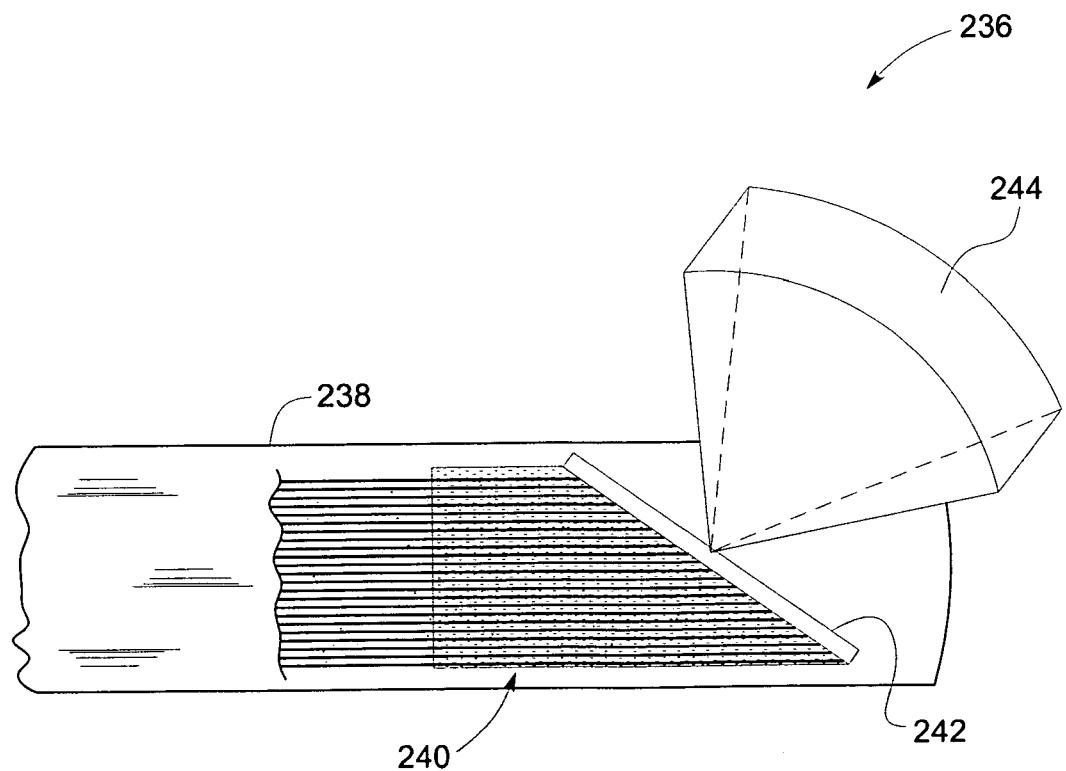
FIG. 20 is a perspective view of an oblique viewing probe including an oblique viewing transducer assembly, in accordance with aspects of the present technique.

Turning to FIG. 20, a perspective view 236 of an exemplary oblique viewing probe including an oblique viewing transducer assembly 240 having the composite structure of z-axis interconnect is illustrated. The oblique viewing transducer assembly is shown as having a transducer array 242. As previously described with reference to FIGS. 14-15, the oblique viewing transducer assembly 240 may be disposed inside an oblique viewing probe 238. Reference numeral 244 is representative of an oblique viewing imaging volume of the oblique viewing probe 238.

It may be noted that composite structures of a predetermined shape may be formed by machining or grinding the composite structure of z-axis interconnect. In other words, employing the techniques of forming the composite array of z-axis interconnect described hereinabove, a composite structure of a wide range of desired shapes may be formed. For example, a composite structure of z-axis interconnect having a substantially cylindrical shape or a substantially spherical shape that advantageously allow a relatively wide field of view may be fabricated.

FIG. 21 is a flow chart of exemplary logic 246 for forming a transducer assembly having a composite structure of z-axis interconnect. In accordance with exemplary aspects of the present technique, a method for forming a composite structure of z-axis interconnect for use in an invasive probe is presented. The method starts at step 248 where a plurality of layers of backing material are alternatingly disposed between a plurality of interconnect layers having at least one conductive element patterned thereon. In one embodiment, the plurality of layers of backing material may be alternatingly stacked between a plurality of interconnect layers.

At step 250, the stack of layers of backing material and interconnect layers may be bonded to form a composite structure of z-axis interconnect having a first end and a second end. Accordingly, each of the plurality of interconnect layers and layers of backing material may be subjected to surface treatments to enhance the adhesion between the layers in the stack. In some embodiments, the surface treatments may include metal sputtering, etching, plasma etching, dehydration baking, mechanical roughening, grinding, or combinations thereof.

An epoxy may then be disposed between each of the layers in the stack. In one embodiment, the epoxy may include a B-stageable epoxy. The B-stageable epoxy may then be subject to B-staging. As will be appreciated, B-staging a curable material may include one or more of heating for a predetermined amount of time, optionally under vacuum, removing some or all of a solvent, at least partially solidifying the material, and/or advancing the cure or cross-linking of a curable resin from an uncured state to a partially, but not completely, cured state. In another embodiment, the epoxy may include a B-staged epoxy. Subsequently, the stack having the plurality of layers of backing material and interconnect layers and the epoxy disposed therebetween may by cured by application of heat and/or pressure to bond the plurality of layers to form the interconnect structure having a first end and a second end.

As previously noted, the first end may be configured to facilitate coupling the composite structure to a transducer array having one or more elements, while the second end may be configured to facilitate coupling to electronics or to cabling associated with a cable assembly. Also, the transducer array may include a PZT transducer array or a MUT transducer array. It may also be noted that it may be desirable to grind and polish the first end of the composite structure to enhance the coupling between the transducer array and the composite structure. Additionally, it may be advantageous to metalize the composite structure of z-axis interconnect to facilitate improvement of electrical contact between the composite structure and transducer array.

Furthermore, at step 252, the transducer array may be operatively coupled to the composite structure of z-axis interconnect to form a transducer assembly. The transducer assembly may include one of a forward viewing transducer assembly for use in a forward viewing probe, a side viewing transducer assembly for use in a side viewing probe, or an oblique viewing transducer assembly for use in an oblique viewing probe.

FIG. 22 is a flow chart of exemplary logic 254 for forming a probe, such as an invasive probe, having a composite structure of z-axis interconnect. In accordance with exemplary aspects of the present technique, a method for forming a probe including the composite structure of z-axis interconnect is presented. The method starts at step 256 where a plurality of layers of backing material are alternatingly disposed between a plurality of interconnect layers having at least one conductive element patterned thereon. In one embodiment, the plurality of layers of backing material may be alternatingly stacked between a plurality of interconnect layers.

At step 258, the stack of layers of backing material and interconnect layers may then be bonded to form a composite structure of z-axis interconnect having a first end and a second end. As noted with reference to FIG. 21, an epoxy may be disposed between the layers in the stack. The epoxy may then be cured via application of heat and/or pressure to bond the layers in the stack thereby forming the composite structure of z-axis interconnect. It may also be noted that it may be desirable to grind, polish and metalize the first end of the composite structure to enhance the coupling between the transducer array and the composite structure, as previously noted.

Subsequently, at step 260, the transducer array may be operatively coupled to the composite structure of z-axis interconnect to form a transducer assembly. As noted hereinabove, the transducer assembly may include one of a forward viewing transducer assembly for use in a forward viewing probe, a side viewing transducer assembly for use in a side viewing probe, or an oblique viewing transducer assembly for use in an oblique viewing probe. Also, at step 262, the transducer assembly thus formed may then be positioned inside a probe housing to form a probe having the exemplary composite structure of z-axis interconnect.

The various embodiments of composite structures of z-axis interconnect and method of producing the various embodiments of composite structures advantageously facilitate substantially high density of interconnections, where the density of interconnection is dependent on a minimum spacing between conductive elements on each interconnect layer, and respective thickness of the interconnect layers and layers of backing material. Furthermore, as a substantially large volume of the composite structure is composed of backing material, acoustic performance of the transducer assembly may be dramatically enhanced.

Also, each of the plurality of interconnect layers may be configured to be relatively thin which greatly facilitates bending of the interconnect layers as desired for use in a side viewing transducer assembly. In addition, a relatively small radius of curvature is feasible which advantageously minimizes wasted space in a probe. The design of composite structure of z-axis interconnect is beneficially space efficient. Consequently, the available space within the probe may be used to maximize the aperture of the transducer assembly thereby enhancing the imaging performance of the probe.

Further, employing the techniques of forming the composite structure of z-axis interconnect described hereinabove facilitates building cost-effective probes for use in imaging systems as the composite structures of z-axis interconnect may be mass produced employing currently available standard fabrication methods. Additionally, due to reduction in motors and other moving parts, generation of real-time three-dimensional images may be greatly enhanced. Current systems employ commercially available monoplanar, two-dimensional B-mode ICE imaging, while the invasive probes, such as imaging catheters, described hereinabove greatly facilitate acquisition of true real-time three-dimensional images. Also, probe cabling may be easily mass terminated onto the interconnect layers.

While only certain features of the invention have been illustrated and described herein, many modifications and herein, many modifications and changes will occur to those skilled in the art. It is, therefore, to be understood that the appended claims, therefore, to be understood that the appended claims are intended to cover all such modifications and changes as fall within the true spirit of the invention.

The invention claimed is:

1. A transducer assembly, comprising:
   a composite structure of a z-axis interconnect; and
   a transducer array disposed proximate the composite structure of the z-axis interconnect, wherein the transducer array comprises one or more transducer elements disposed in an array, and wherein the transducer array is in operative association with the composite structure of the z-axis interconnect,
   wherein the transducer assembly is configured for use in an invasive probe.

2. The transducer assembly of claim 1, wherein the invasive probe comprises an imaging catheter, an endoscope, a laparoscope, a surgical probe, a transvaginal probe, a transrectal probe, an intracavity probe, or a probe adapted for interventional procedures.

3. The assembly of claim 1, wherein the composite structure of the z-axis interconnect comprises a plurality of layers of backing material alternatingly arranged between a plurality of interconnect layers, and wherein the plurality of interconnect layers are configured to facilitate coupling the composite structure of z-axis interconnect to the transducer array.

4. The assembly of claim 3, wherein the plurality of layers of backing material and the plurality of interconnect layers are bonded to form the composite structure having a first end and a second end, wherein the first end is configured to facilitate coupling the composite structure to a transducer array having one or more transducer elements and the second end is configured to facilitate coupling the composite structure to a cable assembly or electronics.

5. The assembly of claim 1, wherein the transducer array comprises a lead zirconate titanate array, a micromachined ultrasound array or combinations thereof.

6. The assembly of claim 1, wherein the assembly comprises one of a forward viewing transducer assembly for use in a forward viewing probe, a side viewing transducer assembly for use in a side viewing probe, or an oblique viewing transducer assembly for use in an oblique viewing probe.

7. The assembly of claim 4, wherein a cross-sectional shape of the first end of the composite structure is different from the cross-sectional shape of the second end.

8. The assembly of claim 3, wherein the plurality of layers of backing material and the plurality of interconnect layers are disposed to form a predetermined shape of the composite structure.

9. The assembly of claim 8, wherein the predetermined shape of the composite structure comprises a square, a rectangle, an octagon, a circle, a rhombus, a triangle or combinations thereof.

10. The assembly of claim 3, wherein each of the plurality of interconnect layers comprises a flexible interconnect layer.

11. The assembly, of claim 10, wherein the flexible interconnect layer comprises at least one conductive element disposed on a flexible substrate having a top side and a bottom side, and wherein the at least one conductive element is configured to facilitate coupling the composite structure to a respective transducer element on a transducer array.

12. The assembly of claim 11, wherein a pitch of conductive elements on an end of the composite structure is configured to match a pitch of the transducer elements on the transducer array.

13. The assembly of claim 12, wherein a pitch of conductive traces on a first end of the composite structure is different from a pitch of conductive traces on a second end of the composite structure, and wherein the pitch of the conductive elements on the second end is configured to match a spacing of connecting elements of a cable assembly or electronics.

14. The assembly of claim 10, wherein the flexible interconnect layers are staggered to facilitate coupling the composite structure to associated cabling or electronics.

15. A transducer assembly, comprising:
- a composite structure of a z-axis interconnect comprising a plurality of layers of backing material alternatingly arranged between a plurality of interconnect layers, wherein the plurality of interconnect layers is configured to facilitate coupling the composite structure of the z-axis interconnect to a transducer array; and
- a transducer array disposed proximate the composite structure of the z-axis interconnect, wherein the transducer array comprises one or more transducer elements disposed in an array, and wherein the transducer array is in operative association with the composite structure of the z-axis interconnect,
- wherein the composite structure of a z-axis interconnect and the transducer assembly are configured for use in an invasive probe.

16. The assembly of claim 15, wherein the plurality of layers of backing material and the plurality of interconnect layers are bonded to form the composite structure having a first end and a second end, wherein the first end is configured to facilitate coupling the composite structure to a transducer array having one or more transducer elements and the second end is configured to facilitate coupling the composite structure to a cable assembly or electronics.

17. The assembly of claim 15, wherein the transducer array comprises a lead zirconate titanate array, a micromachined ultrasound array or combinations thereof.

18. The assembly of claim 15, wherein the assembly comprises one of a forward viewing transducer assembly for use in a forward viewing probe, a side viewing transducer assembly for use in a side viewing probe, or an oblique viewing transducer assembly for use in an oblique viewing probe.

* * * * *